(12) United States Patent
Brady et al.

(10) Patent No.: US 11,160,578 B2
(45) Date of Patent: Nov. 2, 2021

(54) MECHANICAL LOCKOUT FOR ULTRASONIC SURGICAL INSTRUMENT

(71) Applicant: ETHICON LLC, Guaynabo, PR (US)

(72) Inventors: John E. Brady, Liberty Township, OH (US); Alexander R. Cuti, Cincinnati, OH (US); Demetrius N. Harris, Cincinnati, OH (US); Matthew T. Kuhn, Houston, TX (US); Cameron D. McLain, Cincinnati, OH (US); Candice Otrembiak, Loveland, OH (US)

(73) Assignee: Cilag GmbH International, Zug (CH)

( * ) Notice: Subject to any disclaimer, the term of this patent is extended or adjusted under 35 U.S.C. 154(b) by 360 days.

(21) Appl. No.: 15/951,811

(22) Filed: Apr. 12, 2018

(65) Prior Publication Data
US 2019/0314050 A1    Oct. 17, 2019

(51) Int. Cl.
*A61B 17/32* (2006.01)
*A61B 90/00* (2016.01)
*A61B 17/00* (2006.01)

(52) U.S. Cl.
CPC ...... *A61B 17/320068* (2013.01); *A61B 90/03* (2016.02); *A61B 2017/00398* (2013.01); *A61B 2017/00734* (2013.01); *A61B 2017/320074* (2017.08); *A61B 2017/320095* (2017.08)

(58) Field of Classification Search
None
See application file for complete search history.

(56) References Cited

U.S. PATENT DOCUMENTS

| | | | |
|---|---|---|---|
| 5,322,055 A | 6/1994 | Davison et al. |
| 5,873,873 A | 2/1999 | Smith et al. |
| 5,980,510 A | 11/1999 | Tsonton et al. |

(Continued)

FOREIGN PATENT DOCUMENTS

| | | | |
|---|---|---|---|
| EP | 1 199 040 A2 | 4/2002 |
| EP | 2 870 938 A1 | 5/2015 |

(Continued)

OTHER PUBLICATIONS

U.S. Appl. No. 61/410,603, entitled "Energy-Based Surgical Instruments," filed Nov. 5, 2010.

(Continued)

*Primary Examiner* — Martin T Ton
(74) *Attorney, Agent, or Firm* — Frost Brown Todd LLC

(57) ABSTRACT

An ultrasonic surgical instrument that includes an ultrasonic transducer, a handle assembly supporting the ultrasonic transducer, a clamp arm assembly, and a mechanical lockout assembly. The handle assembly includes a housing and an ultrasonic blade acoustically coupled with the ultrasonic transducer. The clamp arm assembly includes a clamp arm. The mechanical lockout assembly is configured to switch between at least an unlocked configuration and a locked configuration. In the locked configuration, the handle assembly and the clamp arm assembly are not completely coupled together and the operator is physically prevented from activating the instrument using an operator input feature. In the unlocked configuration, the clamp arm assembly and the shaft assembly are completely coupled together and the operator is able to activate the instrument using the operator input feature.

19 Claims, 10 Drawing Sheets

(56) References Cited

U.S. PATENT DOCUMENTS

| | | | |
|---|---|---|---|
| 6,325,811 | B1 | 12/2001 | Messerly |
| 6,773,444 | B2 | 8/2004 | Messerly |
| 6,783,524 | B2 | 8/2004 | Anderson et al. |
| 8,663,220 | B2 | 3/2014 | Wiener et al. |
| 9,681,884 | B2 | 6/2017 | Clem et al. |
| 10,368,892 | B2 | 8/2019 | Stulen et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2010/0069940 | A1 | 3/2010 | Miller et al. |
| 2011/0015660 | A1 | 1/2011 | Wiener et al. |
| 2011/0087212 | A1 | 4/2011 | Aldridge et al. |
| 2012/0029546 | A1 | 2/2012 | Robertson |
| 2012/0112687 | A1 | 5/2012 | Houser et al. |
| 2012/0116265 | A1 | 5/2012 | Houser et al. |
| 2013/0324991 | A1* | 12/2013 | Clem ............. A61B 17/320068 606/33 |
| 2014/0005701 | A1 | 1/2014 | Olson et al. |
| 2014/0114334 | A1 | 4/2014 | Olson et al. |
| 2014/0330298 | A1* | 11/2014 | Arshonsky ........... A61B 17/295 606/169 |
| 2015/0080924 | A1 | 3/2015 | Stulen et al. |
| 2015/0080925 | A1 | 3/2015 | Schulte et al. |
| 2015/0141981 | A1 | 5/2015 | Price et al. |
| 2015/0305763 | A1* | 10/2015 | Houser ................ H02J 7/0047 606/1 |
| 2017/0000541 | A1 | 1/2017 | Yates et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0132926 | A1 | 5/2018 | Asher et al. |

FOREIGN PATENT DOCUMENTS

| | | |
|---|---|---|
| EP | 3 225 176 A1 | 10/2017 |
| WO | WO 2017/100412 A1 | 6/2017 |

OTHER PUBLICATIONS

U.S. Appl. No. 62/363,411, entitled "Surgical Instrument with Dual Mode End Effector," filed Jul 18, 2016.
U.S. Appl. No. 15/644,930, entitled "Acoustic Drivetrain with External Collar at Nodal Position," filed Jul. 10, 2017.
U.S. Appl. No. 15/644,944, entitled "Features to Couple Acoustic Drivetrain Components in Ultrasonic Surgical Instrument," filed Jul. 10, 2017.
U.S. Appl. No. 15/951,747, entitled "Electrical Lockout for Ultrasonic Surgical Instrument," filed Apr. 12, 2018.
U.S. Appl. No. 15/951,773, entitled "Mechanical Lockout for Ultrasonic Surgical Instrument," filed Apr. 12, 2018.
U.S. Appl. No. 15/951,788, entitled "Mechanical Lockout for Ultrasonic Surgical Instrument," filed Apr. 12, 2018.
European Search Report, Extended, and Written Opinion dated Jul. 17, 2019 for Application No. 19168695.5, 8 pgs.
European Search Report, Extended, and Written Opinion dated Jul. 5, 2019 for Application No. EP 19168712.8, 8 pgs.
European Search Report, Extended, and Written Opinion dated Jul. 3, 2019 for Application No. EP 19168735.9, 8 pgs.
European Search Report, Extended, and Written Opinion dated Jul. 11, 2019 for Application No. EP 19168796.1, 8 pgs.
International Search Report and Written Opinion dated Jul. 3, 2019 for Application No. PCT/IB2019/053002, 15 pgs.
International Search Report and Written Opinion dated Jul. 11, 2019 for Application No. PCT/IB2019/053004, 12 pgs.
International Search Report and Written Opinion dated Jul. 11, 2019 for Application No. PCT/IB2019/053008, 12 pgs.
International Search Report and Written Opinion dated Jul. 17, 2019 for Application No. PCT/IB2019/053009, 11 pgs.
U.S. Appl. No. 15/951,747.
U.S. Appl. No. 15/951,773.
U.S. Appl. No. 15/951,788.

* cited by examiner

MECHANICAL LOCKOUT FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2017, the disclosure of which is incorporated by reference herein; U.S. Pub. No. 2010/0069940, entitled "Ultrasonic Device for Fingertip Control," published Mar. 18, 2010, issued as U.S. Pat. No. 9,023,017 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,391,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1A:
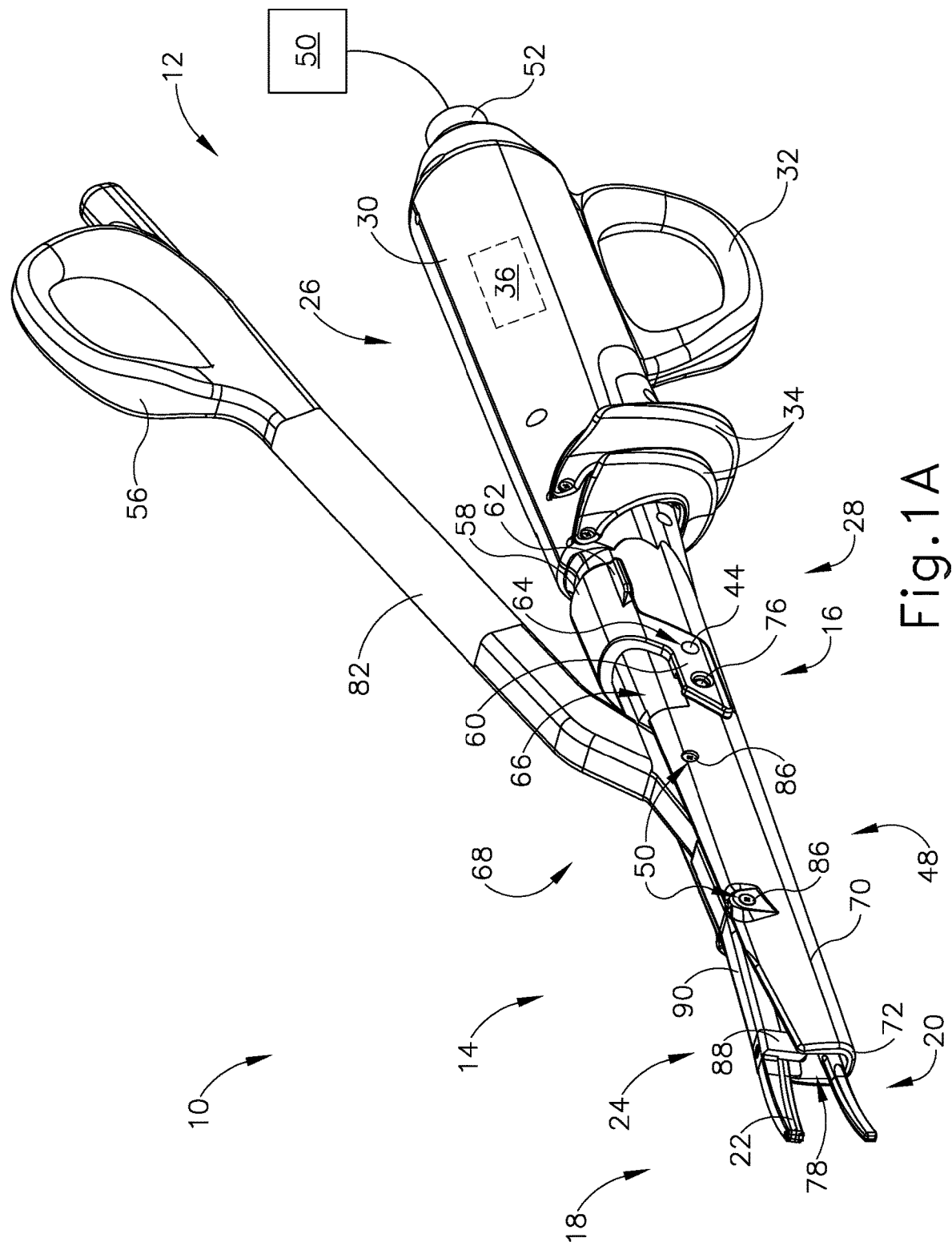
FIG. 1A depicts a perspective view of a first exemplary surgical instrument, with an end effector of the instrument in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Ultrasonic Surgical Instrument for Surgical Procedures

Figure 1B:
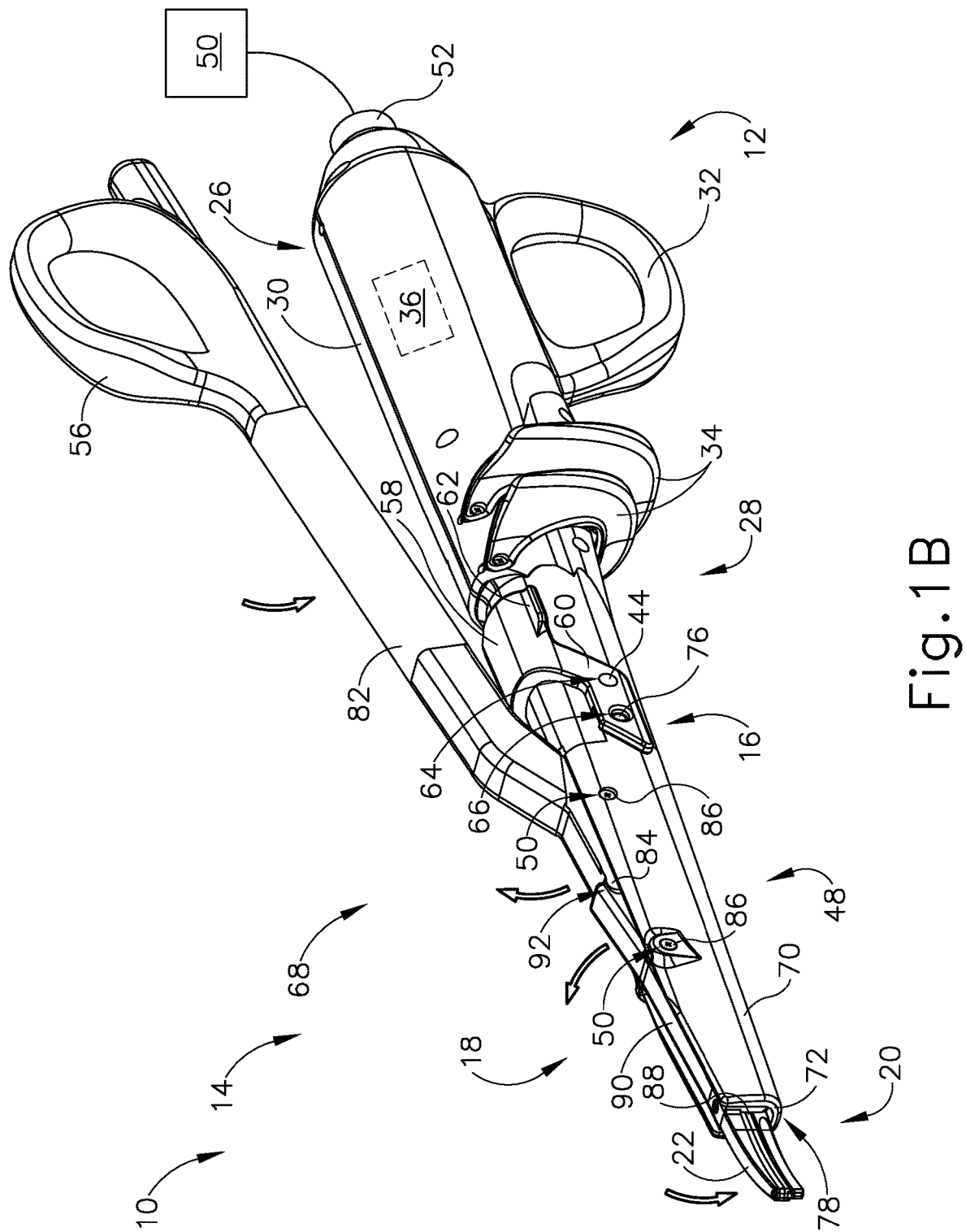
FIG. 1B depicts a perspective view of the instrument of FIG. 1A, with the end effector in a closed configuration.
Figure 2:
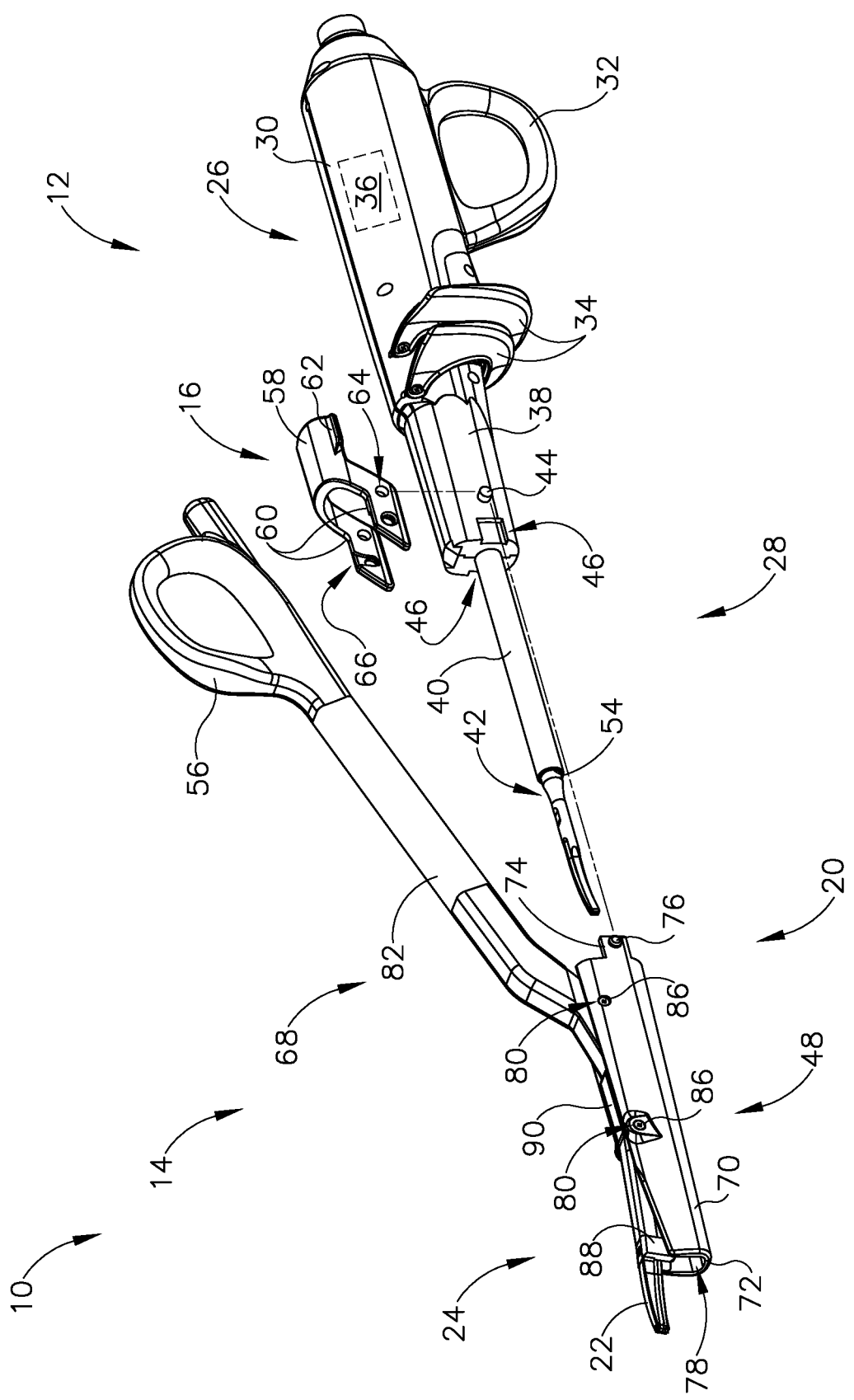
FIG. 2 depicts an exploded perspective view of the instrument of FIG. 1A.

FIGS. 1A-2 illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. In addition, or in the alternative, at least part of instrument (10) may be constructed and operable in accordance with at least some of the teachings of U.S. patent application Ser. No. 15/284,837, entitled "Surgical Instrument with Dual Mode End Effector and Compound Lever with Detents," filed Oct. 4, 2016, issued as U.S. Pat. No. 11,020,200 on Jun. 1, 2021, the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Instrument (10) in the present example includes a first modular assembly (12), a second modular assembly (14), and a coupling member (16). As will be described in greater detail below, coupling member (16) may selectively attach first modular assembly (12) with second modular assembly (14) in order to form instrument (10) with an end effector (18). As best seen in FIGS. 1A-1B, end effector (18) comprises an ultrasonic blade (20) and a clamp pad (22) of a clamp pad assembly (24).

Additionally, as will be described in greater detail below, selected portions of second modular assembly (14) may actuate relative to first modular assembly (12), when properly attached with each other, in order to actuate end effector (18) from an open configuration (FIG. 1A), to a closed configuration (FIG. 1B). The ability to selectively attach and detach second modular assembly (14) with first modular assembly (12) may provide additional benefits of reusability of either modular assembly (12, 14). For instance, different kinds of first modular assemblies (12) may be used with second modular assembly (14) to provide different kinds of surgical instruments. Similarly, different kinds of second modular assemblies (14) may be used with first modular assembly (12) to provide different kinds of surgical instruments. Additionally, moving components of second modular assembly (14) may be housed within static components of second modular assembly (14), which may provide additional advantages, some of which are described below while others will be apparent to one having ordinary skill in the art in view of the teachings herein.

First modular assembly (12) includes a handle assembly (26), a shaft assembly (28) extending distally from handle assembly (26), and ultrasonic blade (20) extending distally from shaft assembly (28). Handle assembly (26) includes a body (30), a finger grip ring (32), a pair of buttons (34) distal to finger grip ring (32), and an ultrasonic transducer assembly (36) housed within body (30).

Shaft assembly (28) includes a proximal outer sheath (38) extending distally from body (30), a tube (40) extending distally from proximal outer sheath (38), and a waveguide (42) extending within and through both proximal outer sheath (38) and tube (40). Proximal outer sheath (38) includes a pair of protrusions (44). Additionally, proximal outer sheath (38) defines a pair of recesses (46). As will be described in greater detail below, recesses (46) are dimensioned to mate with a portion of distal outer sheath (48) while protrusions (44) are configured to pivotally couple proximal outer sheath (38) with coupling member (16). Both protrusions (44) and recesses (46) may help couple first modular assembly (12) with second modular assembly (14).

Proximal outer sheath (38) may be fixed relative to body (30), while tube (40) may be fixed relative to proximal outer sheath (38). As will be described in greater detail below, waveguide (42) may attach to transducer assembly (36) and be supported by portions of proximal outer sheath (38) and tube (40). Ultrasonic blade (20) may be unitarily connected to waveguide (42), and also extend distally from waveguide (42). As will be described in greater detail below, waveguide (42) is operable to connect to ultrasonic transducer assembly (36) in order to provide acoustic communication between ultrasonic blade (20) and transducer assembly (36).

Transducer assembly (36) is housed within body (30) of handle assembly (26). As seen in FIGS. 1A-1B, transducer assembly (36) is coupled with a generator (50) via a plug (52). Transducer assembly (36) receives electrical power from generator (50) and converts that power into ultrasonic vibrations through piezoelectric principles. Generator (50) may include a power source and control module that is configured to provide a power profile to transducer assembly (36) that is particularly suited for the generation of ultrasonic vibrations through transducer assembly (36). Generator (50) may also be configured to provide a power profile that enables end effector (18) to apply RF electrosurgical energy to tissue.

By way of example only, generator (50) may comprise a GEN 300 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (50) may be integrated into handle assembly (26), and that handle assembly (26) may even include a battery or other on-board power source such that plug (52) is omitted. Still other suitable forms that generator (50) may take, as well as various features and operabilities that generator (50) may provide, will be apparent to those of ordinary skill in the art in view of the teachings herein.

Ultrasonic vibrations that are generated by transducer assembly (36) are communicated along acoustic waveguide (42) when properly coupled. Waveguide (42) is mechanically and acoustically coupled with transducer assembly (36). Waveguide (42) extends through shaft assembly (28) to reach ultrasonic blade (20). Waveguide (42) may be secured to proximal outer sheath (38) and/or body (30) via a pin (not shown) extending through waveguide (42) and proximal outer sheath (38). Pin may help ensure waveguide (42) remains longitudinally and rotationally fixed relative to the rest of shaft assembly (28) when waveguide (42) is in a deactivated state (i.e. not vibrating ultrasonically).

Additionally, waveguide (42) may be supported by tube (40) via seals (54) located between an interior of tube (40) and an exterior of waveguide (42). Seals (54) may also prevent unwanted matter and fluid from entering portions of tube (40) housing waveguide (42). Pin (not shown) and seals (54) are located at positions along the length of waveguide (42) corresponding to nodes associated with resonant ultrasonic vibrations communicated through waveguide (42). Therefore, contact between waveguide (42) and pin (not shown), as well as contact between waveguide (42) and seals (54) may not affect ultrasonic vibrations communicated through waveguide (42).

When ultrasonic blade (20) is in an activated state (i.e., vibrating ultrasonically), ultrasonic blade (20) is operable to effectively cut through and seal tissue, particularly when the tissue is being clamped between clamp pad (22) and ultrasonic blade (20). It should be understood that waveguide (42) may be configured to amplify mechanical vibrations transmitted through waveguide (42). Furthermore, waveguide (42) may include features operable to control the gain of the longitudinal vibrations along waveguide (42) and/or features to tune waveguide (42) to the resonant frequency of the system.

In the present example, the distal end of ultrasonic blade (20) is located at a position corresponding to an anti-node associated with resonant ultrasonic vibrations communicated through waveguide (42), in order to tune the acoustic assembly to a preferred resonant frequency $f_o$ when the acoustic assembly is not loaded by tissue. When transducer assembly (36) is energized, the distal end of ultrasonic blade (20) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (36) of the present example is activated, these mechanical oscillations are transmitted through the waveguide (42) reach ultrasonic blade (20), thereby providing oscillation of ultrasonic blade (20) at the resonant ultrasonic frequency. Thus, when tissue is secured between ultrasonic blade (20) and clamp pad (22), the ultrasonic oscillation of ultrasonic blade (20) may simultaneously sever the tissue and denature the proteins in adjacent tissue cells, thereby providing a coagulative effect with relatively little thermal spread.

In some versions, an electrical current may also be provided through ultrasonic blade (20) and/or clamp pad (22) to also seal the tissue. It should therefore be understood that instrument (10) may also be configured to provide radiofrequency (RF) energy to a surgical site via end effector (18). By way of example only, an operator may rely mainly on the use of ultrasonic energy from blade (20) to sever tissue that is captured between ultrasonic blade (20) and clamp pad (22). The operator may further rely on the use of RF energy from end effector (18) to seal the severed tissue. Of course, it will be understood that the ultrasonic energy from blade (20) may seal tissue to some degree, such that the RF energy from end effector (18) may supplement the sealing that would already be provided from the ultrasonic energy. It will also be understood that there may be instances where the operator may wish to simply use end effector (18) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (34) to selectively activate transducer assembly (36) to thereby activate ultrasonic blade (20). In the present example, two buttons (34) are provided. In some versions, one button (34) is provided for activating ultrasonic blade (20) at a first power profile (e.g., a first frequency and/or first amplitude) and another button (34) is provided for activating ultrasonic blade (20) at a second power profile (e.g., a second frequency and/or second amplitude). In some other versions, one button (34) is provided for activating ultrasonic blade (20) with ultrasonic energy, and the other button (34) is provided for activating end effector (18) with RF energy. In some other versions, one button (34) is operable to activate ultrasonic blade (20) with ultrasonic energy while simultaneously activating end effector (18) with RF energy; while the other button (34) is only operable to activate ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while still activating ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while ceasing activation of ultrasonic blade (20) with ultrasonic energy. In some other versions, at least one button (34) is operable to initially activate end effector (18) with RF energy, then based on one or more other conditions (e.g., time, measured impedance, etc.) while button (34) remains activated, eventually activating ultrasonic blade (20) with ultrasonic energy while ceasing activation of end effector (18) with RF energy.

It should be understood that any other suitable number of buttons and/or otherwise selectable power levels and/or power modalities may be provided. For instance, a foot pedal may be provided to selectively activate transducer assembly (36).

Buttons (34) of the present example are positioned such that an operator may readily fully operate instrument (10) with a single hand. For instance, when first and second modular assemblies (12, 14) are coupled, the operator may position their thumb in thumb grip ring (56), position their ring finger in finger grip ring (32), position their middle finger about body (30), and manipulate buttons (34) using their index finger. Of course, any other suitable techniques may be used to grip and operate instrument (10), and buttons (34) may be located at any other suitable position.

As mentioned above, and as will be described below, coupling member (16) is configured to selectively couple first modular assembly (12) with second modular assembly (14). As best seen in FIG. 2, coupling member (16) comprises a body (58), a pair of resilient arms (60), and a pair of grips (62) extending from body (58). Resilient arms (60) each define a respective pivot bore (64) and a locking assembly (66). Resilient arms (60) are spaced apart from each other in order to receive proximal outer sheath (38) and to snap-fit pivot bores (64) with respective protrusions (44). Coupling member (16) is configured to pivotally connect with proximal outer sheath (38) via pivot bores (64) and protrusions (44). While in the current example, coupling member (16) and proximal outer sheath (38) are pivotally coupled via snap-fitting, any other type of suitable connection may be used as would be apparent to one having ordinary skill in the art in view of the teachings herein. For example, protrusions (44) may be extendable relative to proximal outer sheath (38) in order to pivotally couple with pivot bore (64) of coupling member (16). Grips (62) may be positioned on body (58) such that an operator may easily rotate coupling member (16) relative to proximal outer sheath (38) via grips (62). As will be described in greater detail below, locking assembly (66) is configured to rotate about pivot bore (64) and protrusions (44) in order to selectively couple with portions of first modular assembly (14).

While coupling member (16) in the current example is used to connect first modular assembly (12) with second modular assembly (14), it should be understood that coupling member (16) may be incorporated into any suitable type of modular assembly that would be apparent to one having ordinary skill in the art in view of the teachings herein. For example, coupling member (16) may be modified to couple different modular clamp arm assemblies with first modular assembly (12) where the different modular clamp arm assemblies include clamp arm assemblies such as those taught in U.S. patent application Ser. No. 15/284,855, entitled "Surgical Instrument with Dual Mode End Effector and Modular Clamp Arm Assembly," filed Oct. 4, 2016, issued as U.S. Pat. No. 10,893,914 on Jan. 10, 2021, the disclosure of which is incorporated by reference herein. Thus, one modular clamp arm assembly that may be coupled with first modular assembly (12) may provide pivotal motion of a clamp arm at one side of ultrasonic blade (20) while the other modular clamp arm assembly that may be coupled with first modular assembly (12) may provide pivotal motion of a clamp arm at the other side of ultrasonic blade (20). Other suitable kinds of clamp arm assemblies that may be used to provide different kinds of second modular assemblies (14) will be apparent to those of ordinary skill in the art in view of the teachings herein.

Second modular assembly (14) includes a clamp arm assembly (68), clamp pad assembly (24), and a distal outer sheath (48). As will be described in greater detail below, distal outer sheath (48) is configured to couple with both coupling member (16) and proximal outer sheath (38) in order to selectively couple first modular assembly (12) with second modular assembly (14). It other words, when properly coupled, proximal outer sheath (38) and distal outer sheath (48) may be fixed relative to one another. As will also be described in greater detail below, clamp arm assembly (68) and clamp pad assembly (24) are both pivotally coupled with distal outer sheath (48). Additionally, clamp arm assembly (68) and clamp pad assembly (24) are dimensioned to mesh with each other such that rotation of one assembly (24, 68) relative to distal outer sheath (48) causes rotation of the other assembly (24, 68) relative to distal outer sheath (48). In other words, clamp pad assembly (24) and clamp arm assembly (68) are capable of rotating each other relative to distal outer sheath (48).

Distal outer sheath (48) includes a U-shaped body (70) extending from a distal face (72) and terminating in a pair of proximally presented projections (74). Proximally presented projections (74) each include a lateral protrusion (76) extending away from U-shaped body (70). U-shaped body (70) defines a longitudinal pathway (78) and a plurality of bores (80). U-shaped body (70) and longitudinal pathway (78) are dimensioned to receive tube (40) and to rotationally house a portion of clamp arm assembly (68) and clamp pad assembly (24). In particular, U-shaped body (70) may be inserted over ultrasonic blade (20) and tube (40) such that tube (40) will rest under clamp arm assembly (68) and clamp pad assembly (24). Tube (40) may protect waveguide (42) such that clamp arm assembly (68) and clamp pad assembly (24) do not contact adjacent portions of waveguide (42).

As shown in FIG. 2, proximally presented projections (74) are configured to be inserted into recesses (46) defined by proximal outer sheath (38). When proximally presented projections (74) are inserted into recesses (46), distal outer sheath (48) may not rotate relative to proximal outer sheath (38) about a longitudinal axis defined by tube (40). Therefore, proximally presented projections (74) may mate with recesses (46) in order to rotationally fix distal outer sheath (48) relative to proximal outer sheath (38).

Once distal outer sheath (48) is rotationally fixed relative to proximal outer sheath (38), an operator may rotate coupling member (16) such that locking assembly (66) snap-fits with lateral protrusions (76). In particular, an operator may rotate coupling member (16) about protrusions (44) such that lateral protrusions (76) cam against resilient arms (60). As a result, resilient arms (60) are flexed outwardly away from proximally presented projections (74). An operator may further rotate coupling member (16) about protrusions (44). The resilient nature of resilient arms (60) allows resilient arms (60) to return to a relaxed position such that lateral protrusions (76) rest within locking assembly (66). With locking assembly (66) of coupling member (16) fully attached, distal outer sheath (48) is longitudinally fixed relative to proximal outer sheath (38), thereby coupling first modular assembly (12) with second modular assembly (14).

If an operator wishes to decouple first modular assembly (12) with second modular assembly (14), an operator may grasp grips (62) to rotate coupling member (16) in the opposite direction about protrusions (44) in order to flex resilient arms (60) to pop out lateral protrusions (76).

As mentioned above, clamp arm assembly (68) and clamp pad assembly (24) are both pivotally coupled with distal outer sheath (48) such that rotation of one assembly (24, 68) relative to distal outer sheath (48) causes rotation of the other assembly (24, 68) relative to distal outer sheath (48).

Clamp arm assembly (68) includes an elongated arm (82), thumb grip ring (56), a camming protrusion (84) seen in FIG. 1B. Thumb grip ring (56) and elongated arm (82) together provide a scissor grip type configuration in combination with body (30) and finger grip ring (32). Pivot coupling pivotally couples clamp arm assembly (68) with distal outer sheath (48) via pins (86). As will be described in greater detail below, camming protrusion (84) interacts with clamp pad assembly (24) in order to rotate clamp pad assembly (24) in response to rotation of clamp arm assembly (68).

Clamp pad assembly (24) includes clamp pad (24) facing ultrasonic blade (20), a pair of tissue stops (88) located adjacent to ultrasonic blade (20) and proximal to clamp pad (22), an arm (90) defining a camming recess (92) as seen in FIG. 1B. In some versions, clamp pad assembly (24) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (24) may incorporate one or more electrodes that is/are operable to apply RF electrosurgical energy to tissue will be apparent to those of ordinary skill in the art in view of the teachings herein.

In the current example, tissue stops (88) longitudinally align with distal face (72) when end effector (18) is in the closed position. Tissue stops (88) and distal face (72) may cooperate to consistently and simply prevent tissue from inadvertently reaching a proximal position within end effector (18) where ultrasonic energy from blade (20) may not adequately sever or seal the tissue. In providing such prevention, tissue stop (88) may eliminate the need for an operator to visualize proximal region of end effector (18) in order to determine whether the tissue has reached an undesirably proximal position within end effector (18).

Camming protrusion (84) is dimensioned to rotate within camming recess (92) while also contacting camming recess (92). Camming protrusion (84) and camming recess (92) are positioned within distal outer sheath (48). Therefore, as shown between FIGS. 1A-1B, when an operator rotates elongated arm (82) toward distal outer sheath (48), camming protrusion (84) rotates away from distal outer sheath (48). Because camming protrusion (84) is housed within camming recess (92), upward movement of camming protrusion (84) causes upward movement of camming recess (92). Upward movement of camming recess (92) rotates arm (90) such that clamp pad (22) rotates toward ultrasonic blade (20). Therefore, closure of elongated arm (82) of clamp arm assembly (68) toward handle assembly (26) leads to closure of clamp pad (22) toward ultrasonic blade (20). It should therefore be understood that when first modular assembly (12) and second modular assembly (14) are connected, an operator may squeeze thumb grip ring (56) toward body (30) to thereby clamp tissue between clamp pad assembly (24) and ultrasonic blade (20) to compress tissue against ultrasonic blade (20). When ultrasonic blade (20) is activated during such compression, clamp pad assembly (24) and ultrasonic blade (20) cooperate to transect and/or seal the compressed tissue.

In some versions, one or more resilient members are used to bias clamp pad assembly (24) toward the open position shown in FIG. 1A. Of course, any other suitable kind of resilient member may be used as would be apparent to one having ordinary skill in the art in view of the teachings herein, such as a torsion spring. Alternatively, clamp pad assembly (24) need not necessarily be biased toward the open position.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. 8,461,744 on Jun. 11, 2013; U.S. Pub. No. 2012/0112687, issued as U.S. Pat. 9,381,058 on Jul. 5, 2016; U.S. Pub. No. 2012/0116265, now abandoned; U.S. Pub. No. 2014/0005701issued as U.S. Pat. No. 9,393,037 on Jul. 19, 2016; U.S. Pub. No. 2014/0114334issued as U.S. Pat. No. 9,095,367 on Aug. 4, 2015; and/or U.S. Pub. No. 2015/0080925, entitled "Alignment Features for Ultrasonic Surgical Instrument," published Mar. 19, 2015, now abandoned, the disclosure of which is incorporated by reference herein.

II. Alternative Exemplary Ultrasonic Surgical Instruments and Various Mechanical Lockout Assemblies Given that various portions of ultrasonic surgical instrument (10) removably connect together, it may be desirable in various examples to reuse some portions of ultrasonic surgical instrument (10) while replacing others upon reconnection for further use by the surgeon. For example, the first modular assembly (12) in the present example is reusable whereas second modular assembly (14) may be disconnected and replaced with an unused, replacement second modular assembly (14). Since first modular assembly (12) is separable from second modular assembly (14), it is beneficial to ensure that first modular assembly (12) and second modular assembly (14) are correctly and completed assembled prior to use to prevent a malfunction or inadvertent separation of first modular assembly (12) from second modular assembly (14). For at least this reason, it may be desirable to incorporate a lockout assembly that prevents use of instrument (10) when the first modular assembly (12) and second modular assembly (14) are not correctly and completed assembled together.

While the following mechanical lockout assemblies (216, 316, 416, 416') are shown in distinct positions between reusable and replaceable features for removable connection, any of the following mechanical lockout assemblies (216, 316, 416, 416'), it will be appreciated that mechanical lockout assemblies (216, 316, 416, 416') may be incorporated into any surgical instrument described herein, exchanged, or moved so as to make one or more portions of a surgical instrument removable from a remainder of the surgical instrument. Two general forms of mechanical lockout varieties are shown and described below. First, a mechanical lockout assembly that that effectively locks the clamp arm, thereby preventing the operator from clamping on tissue with the end effector. Second, a mechanical lockout assembly that effectively locks the energy control buttons, thereby preventing the operator from activating the ultrasonic blade. As such, mechanical lockout assemblies (216, 316, 416, 416') are intended to cover both energy control button lockouts preventing activation of ultrasonic blade and trigger lockouts preventing closure of clamp arm assembly toward ultrasonic blade. It is also appreciated that one or more of these mechanical lockout assemblies (216, 316, 416, 416') may be used in combination with another mechanical lockout assemblies (216, 316, 416, 416').

The following description provides various examples of mechanical lockout assemblies. Such mechanical lockout assemblies (216, 316, 416, 416') described below may be used with any ultrasonic surgical instrument described above and below and in any of the various procedures described in the various patent references cited herein. To this end, like numbers below indicate like features described above. Except as otherwise described below, ultrasonic surgical instruments (210, 310, 410) described below may be constructed and operable like instruments (10) described above. Certain details of ultrasonic surgical instruments (210, 310, 410) will therefore be omitted from the following description, it being understood that such details are already provided above in the description of instruments (10). Other suitable ways in which various ultrasonic surgical instruments may be used will be apparent to those of ordinary skill in the art in view of the teachings herein.

Similarly, various electrical lockouts may be incorporated into any surgical instrument in conjunction with the following mechanical lockouts (216, 316, 416, 416'). Such electrical lockouts are disclosed in U.S. Application Ser. No. 15,951,747, entitled "Electrical Lockout for Ultrasonic Surgical Instrument," filed on Apr. 12, 2018, published as U.S. Pub. No. 2019/0314054 on Oct. 17, 2019, the disclosure of which is incorporated by reference herein. Other suitable ways in which various ultrasonic surgical instruments may be used will be apparent to those of ordinary skill in the art in view of the teachings herein.

Figure 3:
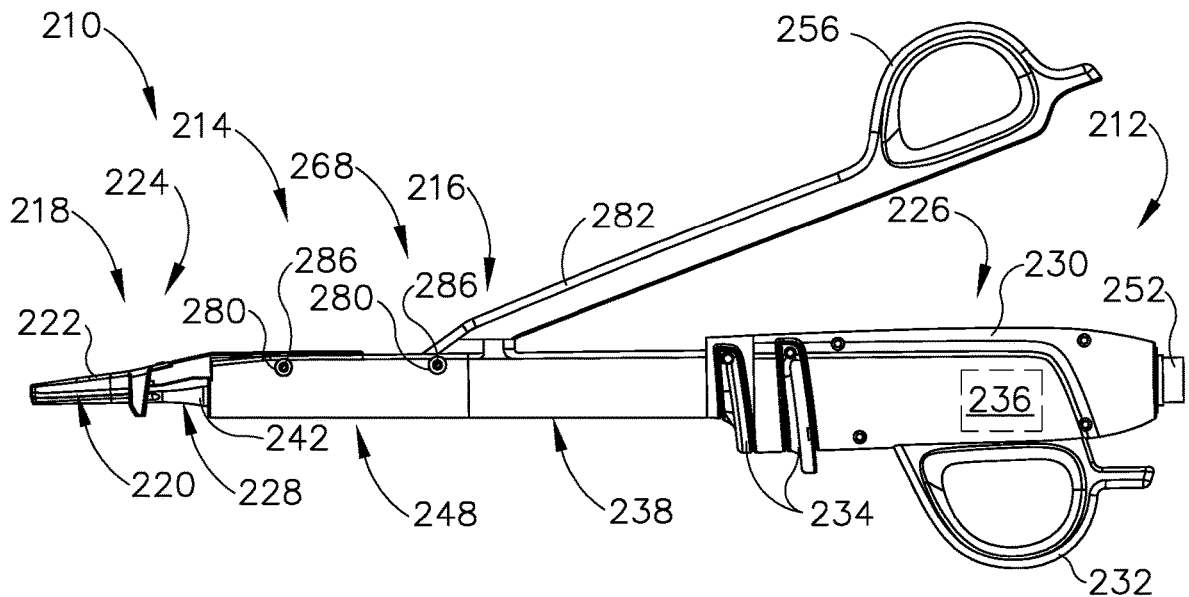
FIG. 3 depicts a schematic side view of a second exemplary ultrasonic surgical instrument.
Figure 4:
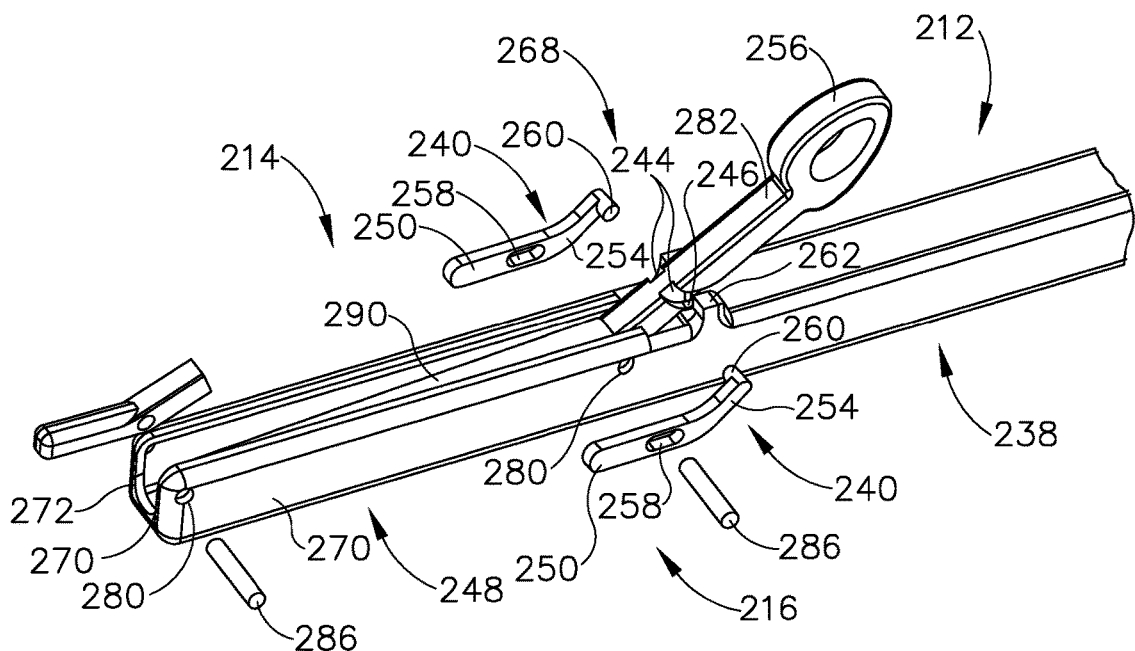
FIG. 4 depicts a schematic partially exploded perspective view of a portion of the instrument of FIG. 3 including a first exemplary mechanical lockout assembly.

A. Second Exemplary Ultrasonic Surgical Instrument Having a First Example of a Mechanical Lockout Assembly FIGS. 3-7 show a second exemplary ultrasonic surgical instrument (210) including a first mechanical lockout assembly (216). As shown in FIGS. 3-4, instrument (210) of the present example comprises a first modular assembly (212), a second modular assembly (214), an end effector (218), an ultrasonic blade (220), a clamp pad (222), a clamp pad assembly (224), a handle assembly (226), a shaft assembly (228), a body (230), a finger grip ring (232), a pair of buttons (234), an ultrasonic transducer (236), a proximal outer sheath (238), a waveguide (242), a distal outer sheath (248), a plug (252), a thumb grip ring (256), a clamp arm assembly (268), a U-shaped body (270), a distal face (272), a longitudinal pathway (278), a plurality of bores (280), an elongated arm (282), a plurality of pins (286), and an arm (290).

With reference to FIG. 3, first modular assembly (212) is configured to be removably coupled with second modular assembly (214). As shown, first modular assembly (212) includes handle assembly (226), ultrasonic transducer (236), energy control buttons (234), and proximal outer sheath (238), with ultrasonic transducer (236) being supported by first modular assembly (212). Waveguide (242) is acoustically coupled with ultrasonic transducer (236). Second modular assembly (214) includes waveguide (242), clamp arm assembly (268), distal outer sheath (248), and at least a portion of end effector (218), where end effector (218) extends distally from a distal end portion of second modular assembly (214).

FIG. 4 shows ultrasonic surgical instrument (210) also including at least one mechanical lockout assembly (216). Mechanical lockout assembly (216) is configured to enable switching between at least a locked configuration and an unlocked configuration. While FIG. 4 shows mechanical lockout assembly (216) including two distinct and separate lockout members (240), more or fewer lockout members (240) are also envisioned, including using only a single lockout member (240).

Figure 5A:
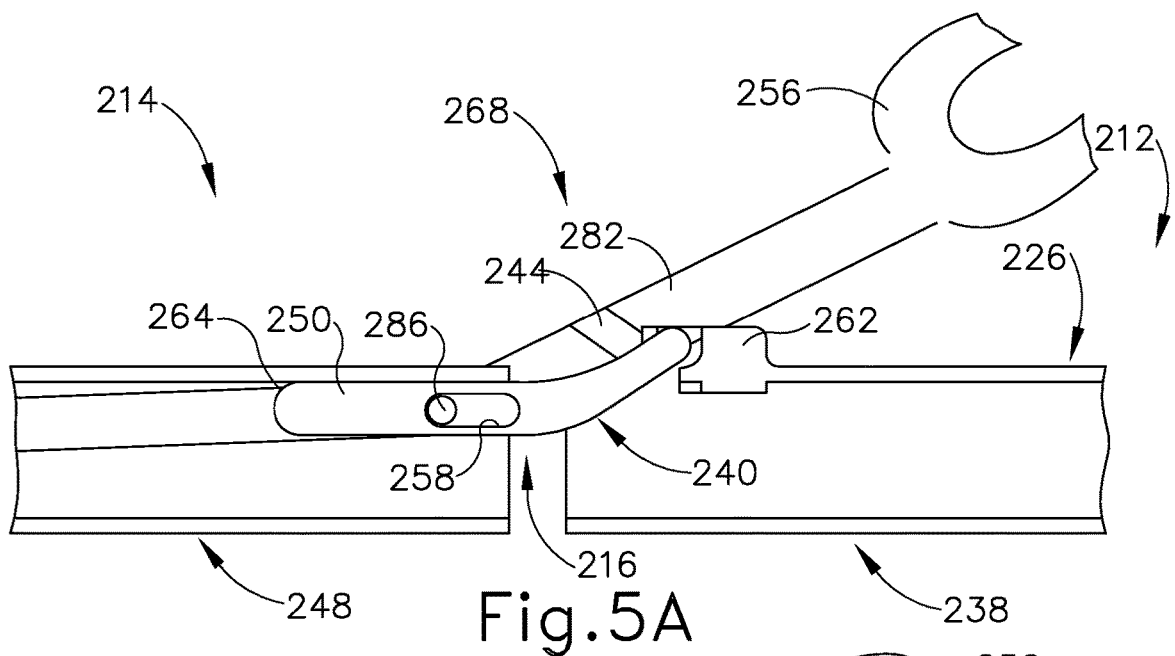
FIG. 5A depicts a schematic sectional view of the instrument similar to FIG. 4 in a locked configuration.
Figure 5B:
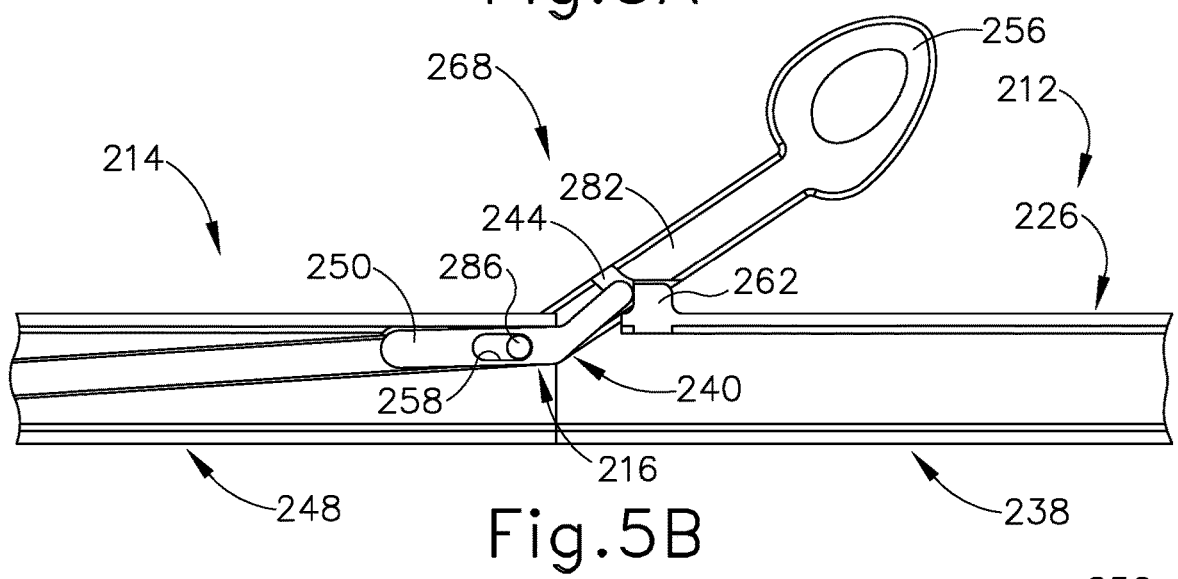
FIG. 5B depicts the schematic sectional view of the instrument similar to FIG. 4, but moving from the locked configuration to an unlocked configuration.
Figure 5C:
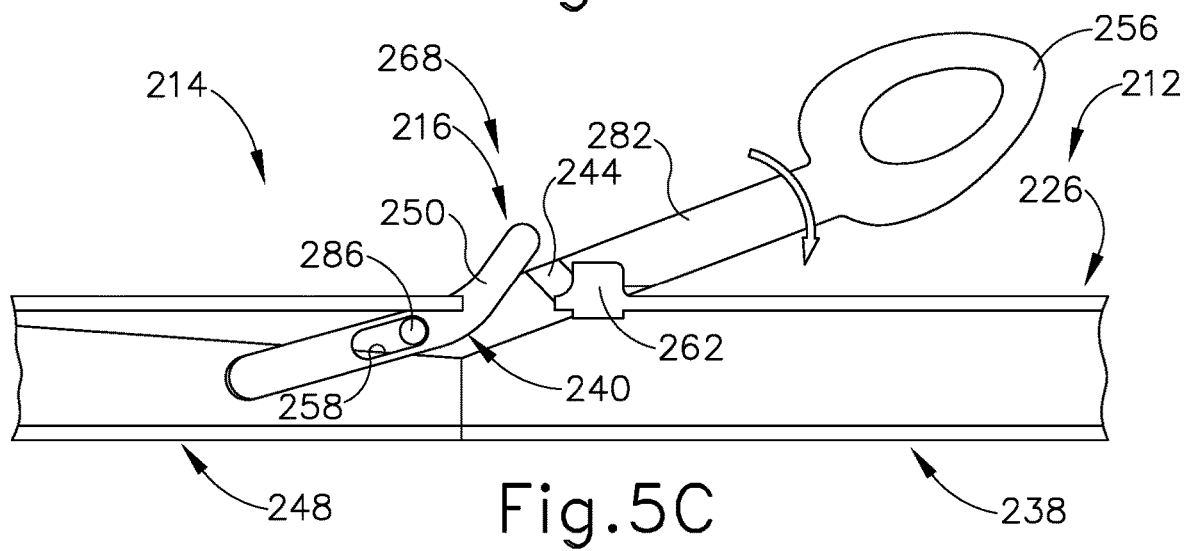
FIG. 5C depicts the schematic sectional view of the instrument similar to FIG. 4, but in the unlocked configuration.
Figure 6:
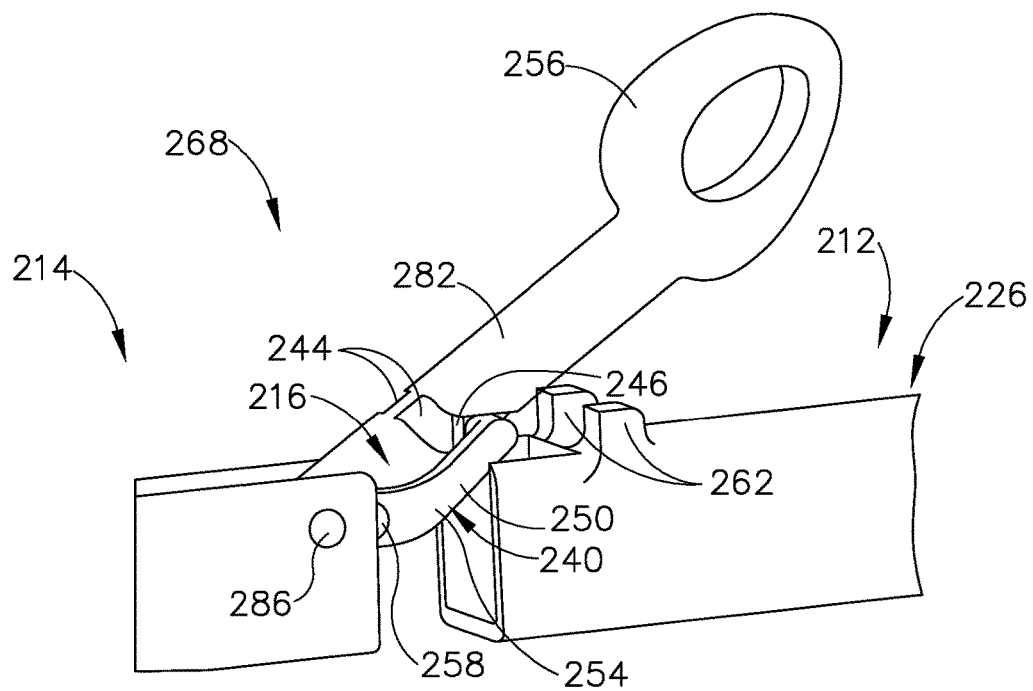
FIG. 6 depicts a schematic perspective view of the instrument similar to FIG. 5A in the locked configuration.
Figure 7:
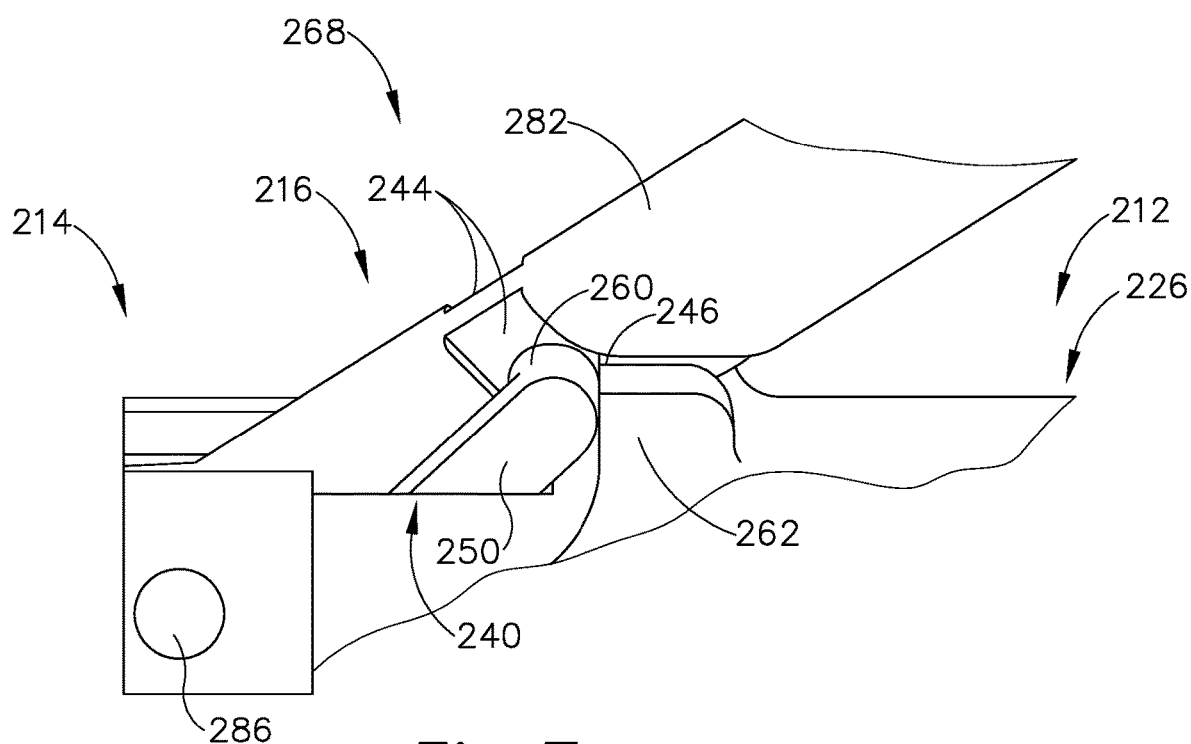
FIG. 7 depicts a schematic perspective view of the instrument similar to FIG. 5B still in the locked configuration, but moving to the unlocked configuration.

As best seen in FIGS. 4-8, clamp arm assembly (268) includes an elongate arm (282) and a thumb grip ring (256). As shown, clamp arm assembly (268) includes at least one cutout portion (244). Lockout member (240) is configured to move from the locked configuration to the unlocked configuration, while being at least partially contained within cutout portions (244). As shown in FIGS. 4, 6 and 7, cutout portions (244) may each include a protrusion (246) to inhibit translation of lockout member (240) while in the locked configuration. As will be described in greater detail below, while in the unlocked configuration, lockout member (240) is not contained within cutout portion (244).

FIG. 4 shows lockout member (240) as including a body (250) with a lockout feature having at least one of a curve (254), a change in angle, a slot (258), or a proximal projection (260) from body (250). Pin (286) pivotably couples distal outer sheath (248) with both clamp arm assembly (268) and lockout member (240). Proximal outer sheath (238) includes a projection (262) that displaces lockout member (240) distally when coupling proximal outer sheath (238) with distal outer sheath (248). As shown, lockout member (240) uses the same rotation point as clamp arm assembly (268).

FIG. 5A shows the locked configuration, where first modular assembly (212) and second modular assembly (214) are partially coupled together such that an operator is physically prevented from actuating clamp arm assembly (268). Mechanical lockout assembly (216) prevents the operator from clamping tissue with end effector (218). In the locked configuration, lockout member (240) prevents actuation of clamp arm assembly (268) due to interference with both elongated arm (282) of clamp arm assembly (268) and distal outer sheath (248). As shown, when the operator attempts to depress clamp arm assembly (268), lockout member (240) hits a top surface of projection (262) adjacent the top of distal outer sheath (248). This prevents clamping of end effector (218) on tissue when instrument (210) is not properly assembled. The operator cannot depress elongated arm (290) while lockout member (240) of mechanical lockout assembly (216) is in place.

FIG. 5B and FIG. 7 show an exemplary unlocking of instrument (210). As proximal outer sheath (238) is coupling with distal outer sheath (248), projection (262) on proximal outer sheath (238) translates lockout member (240) forward, past protrusion (246) on elongated arm (282). This effectively unlocks clamp arm assembly (268). Slot (258) in lockout member (240) allows for proximal displacement of pin (286), such that pin (286) slides within slot (258) allowing elongated arm (282) to pivot. Lockout member (240) translates distally away from projection (262) when moving from the locked configuration to the unlocked configuration.

FIG. 5C shows the unlocked configuration, where proximal outer sheath (238) is completely coupled with distal outer sheath (230), such that the operator is able to activate instrument (210). In the unlocked configuration, clamp arm assembly (268) freely rotates relative to locking member (264) and is not contained within cutout portion (244). Elongated arm (282) may be further depressed after unlocking instrument (210). The operator may fully clamp on tissue with end effector (218) after instrument (210) is fully assembled.

Additionally, in the locked configuration, instrument (210) allows for a method of maintaining the position of elongated arm (282) relative to distal outer sheath (248) to improve ease of assembly by the operator. Mechanical lockout assembly (216) holds elongated arm (282) of clamp arm assembly (268) in a position that will not impede assembly providing an additional benefit.

Figure 8:
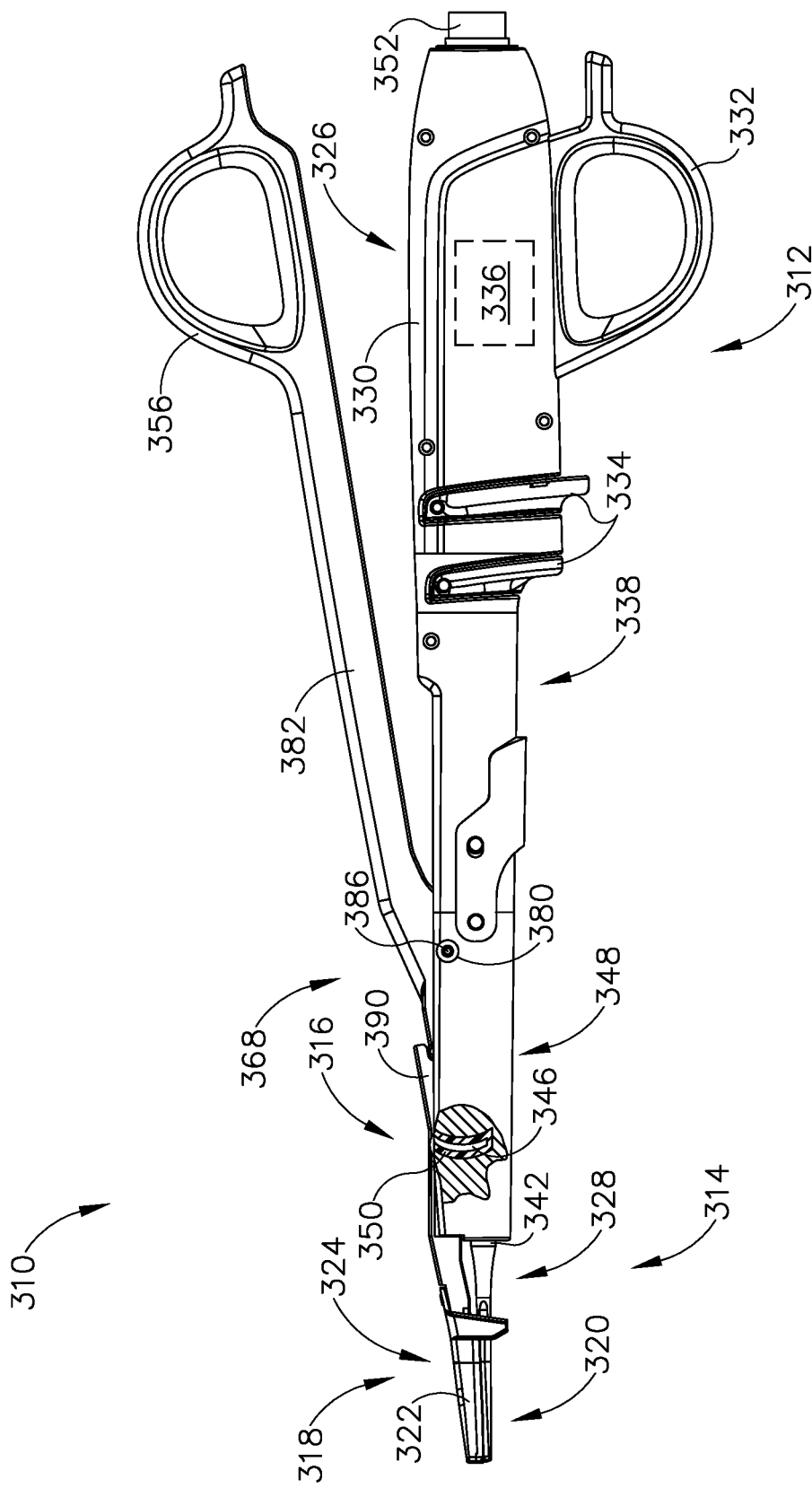
FIG. 8 depicts a schematic side view of a third exemplary ultrasonic surgical instrument in an unlocked configuration, with a portion of the outer sheath being shown in a cutaway to depict a second exemplary mechanical lockout assembly.

B. Third Exemplary Ultrasonic Surgical Instrument Having a Second Example of a Mechanical Lockout Assembly FIGS. 8-10 show a third exemplary ultrasonic surgical instrument (310) including a second mechanical lockout assembly (316). FIG. 8 of the present example shows that instrument (310) comprises a first modular assembly (312), a second modular assembly (314), an end effector (318), an ultrasonic blade (320), a clamp pad (322), a clamp pad assembly (324), a handle assembly (326), a shaft assembly (328), a body (330), a finger grip ring (332), a pair of buttons (334), an ultrasonic transducer (336), a proximal outer sheath (338), a waveguide (342), a distal outer sheath (348), a plug (352), a thumb grip ring (356), a clamp arm assembly (368), a U-shaped body (370), a distal face (372), a longitudinal pathway (378), a plurality of bores (380), an elongated arm (382), a camming protrusion (384), a plurality of pins (386), an arm (390), and a camming recess (392).

FIG. 8 shows first modular assembly (312) configured to be removably coupled with second modular assembly (314). First modular assembly (312) includes handle assembly (326), ultrasonic transducer (336), and proximal outer sheath (338), with ultrasonic transducer (336) being supported by first modular assembly (312). Waveguide (342) is acoustically coupled with ultrasonic transducer (336). Second modular assembly (314) includes waveguide (342), clamp arm assembly (368), distal outer sheath (348), and at least a portion of end effector (318). End effector (318) extends distally from a distal end portion of second modular assembly (214).

With continued reference to FIG. 8, mechanical lockout assembly (316) enables switching between at least an unlocked configuration and a locked configuration. Mechanical lockout assembly (316) includes at least one projection (340) operatively coupled with clamp arm assembly (368). Projection (346), coupled with arm (390), is configured to mate clamp arm assembly (368) with at least one recess (350) in distal outer sheath (348) to ensure proper alignment throughout closing. FIG. 10 shows a top down view of recesses (350) in distal outer sheath (348). While projections (346) and recesses (350) are shown as curvilinear, other shapes are also envisioned.

Figure 9A:
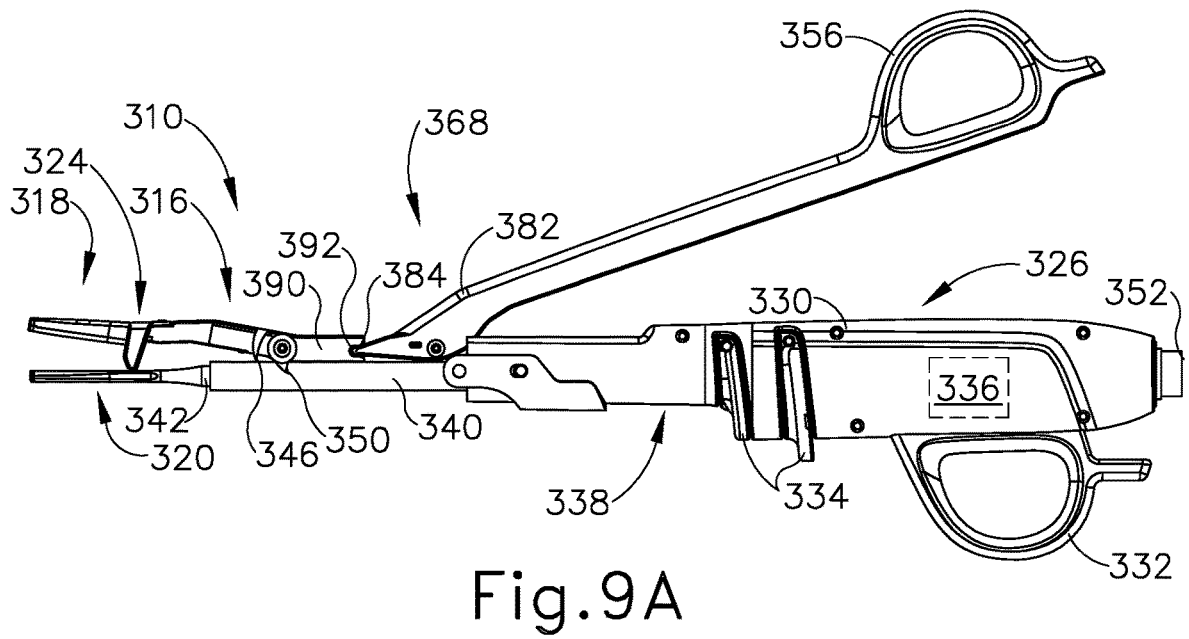
FIG. 9A depicts a schematic side view of the instrument similar to FIG. 8, but in a locked configuration with cutouts in the outer sheath.

FIG. 9A shows instrument (310) in the locked configuration, where first modular assembly (312) and second modular assembly (314) are partially coupled together, such that the operator is physically prevented from activating instrument (310). More specifically, FIG. 9A shows arm (390) pivoted away such that the clamp pad (322) is spaced away from ultrasonic blade (320). Distal outer sheath (348) has been hidden in FIGS. 9A-9B for improved clarity. In the locked configuration, projection (346) is not received by corresponding recess (350) in distal outer sheath (348). As a result, projection (346) prevents the operator from being able to clamp down on tissue with end effector (318). In other words, in the locked configuration, ultrasonic blade (320) and clamp pad (322) are unable to approach each other when projection (346) is not aligned with the recess (350). Unless projection (346) is aligned with recess (350), projection (346) provides a hard stop preventing clamp arm assembly (368) from pivoting toward ultrasonic blade (320). While two recesses (350) are shown to capture two corresponding projections (346), more or fewer projections (346) and corresponding recesses (350) are also envisioned.

Figure 9B:
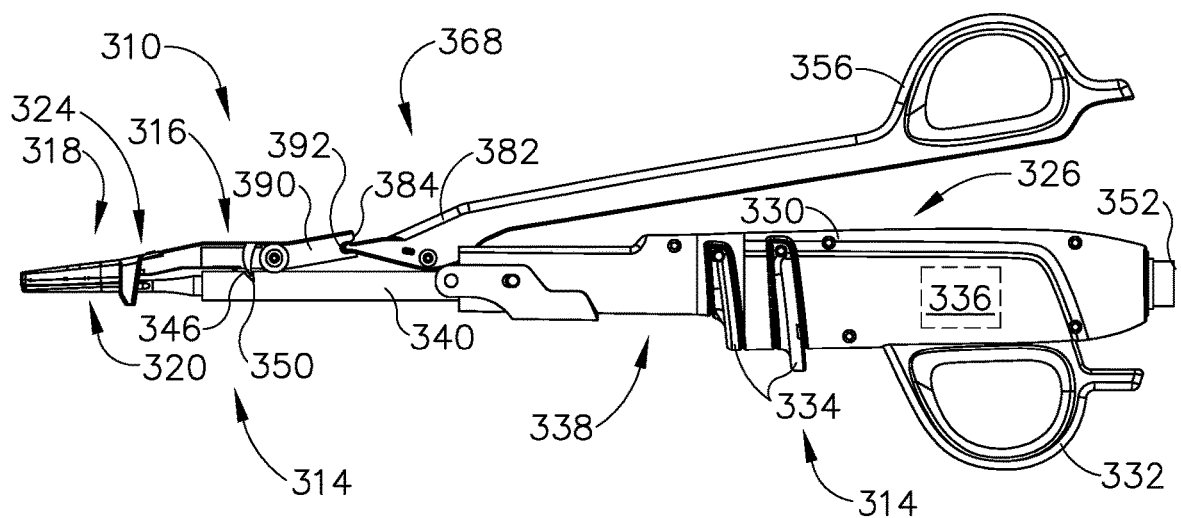
FIG. 9B depicts the schematic side view of the instrument similar to FIG. 9A, but in an unlocked configuration with cutouts in the outer sheath.
Figure 10:
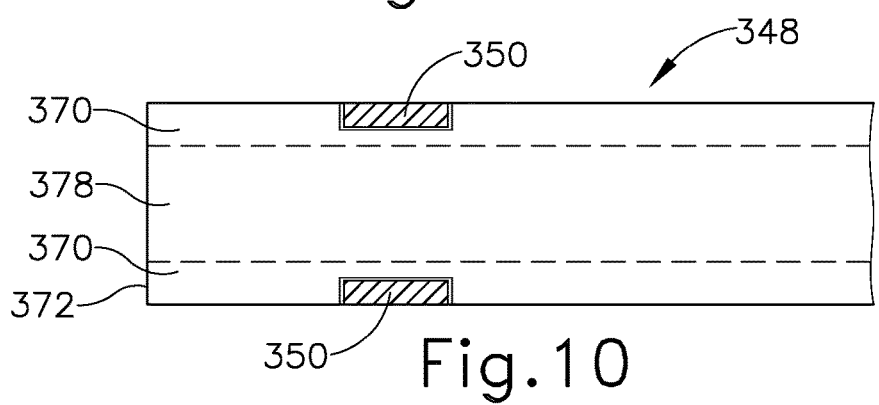
FIG. 10 depicts a schematic top view of the outer sheath and the associated cutouts of FIG. 8.

FIG. 9B shows instrument (310) in the unlocked configuration, where first modular assembly (212) and second modular assembly (314) are completely coupled together and the operator is able to activate instrument (310) using clamp arm assembly (368). In the unlocked configuration, projection (340) is received by corresponding recess (350) in distal outer sheath (348) allowing instrument (10) to be activated. In the unlocked configuration, projection (346) no longer provides a hard stop, thereby allowing clamp arm assembly (368) to pivot towards ultrasonic blade (320). It is beneficial that clamp arm assembly (368) be precisely longitudinally aligned with ultrasonic blade (320).

Figure 11A:
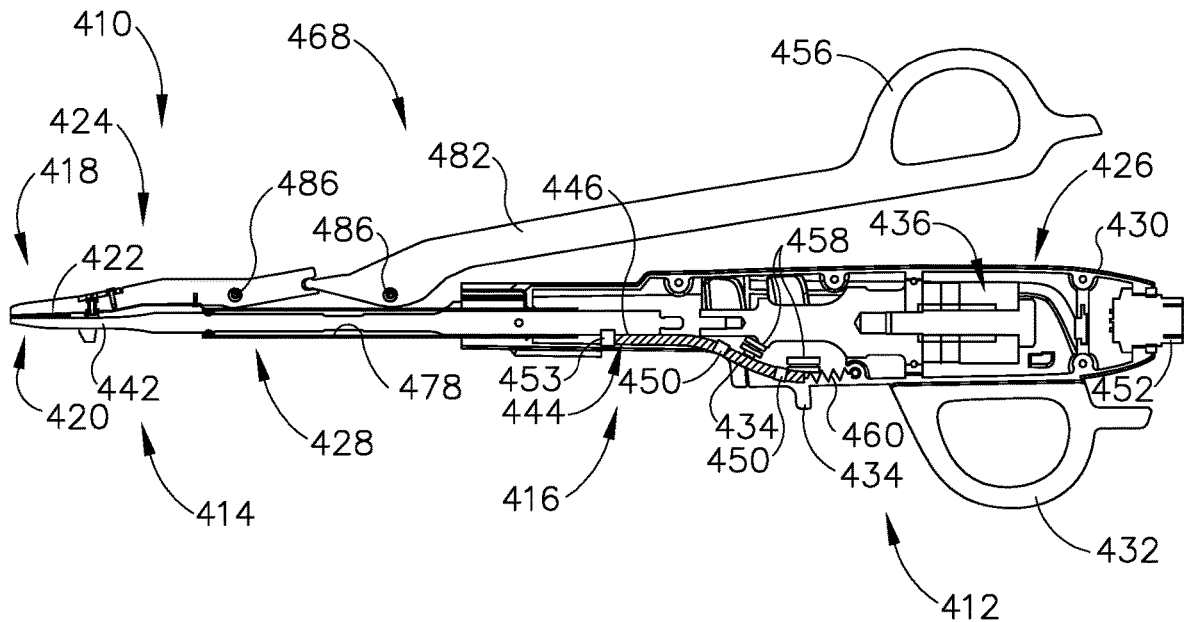
FIG. 11A depicts a schematic side view of a fourth exemplary ultrasonic surgical instrument including a third exemplary mechanical lockout assembly in a locked configuration.
Figure 11B:
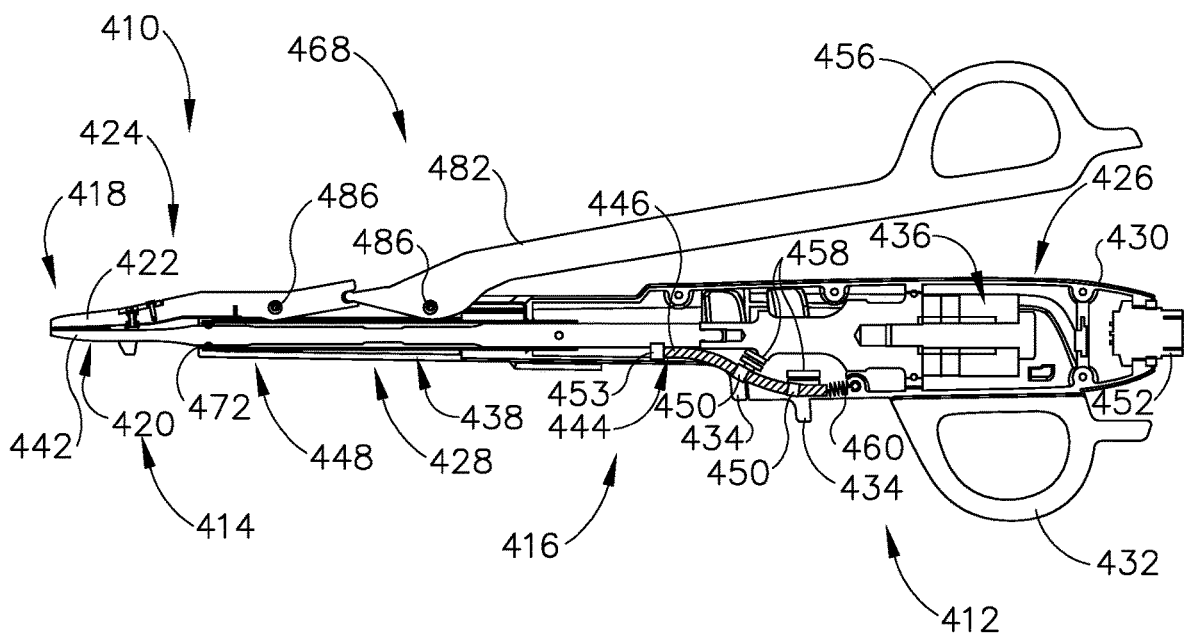
FIG. 11B depicts the schematic side view of the instrument similar to FIG. 11A, but in an unlocked configuration.

C. Fourth Exemplary Ultrasonic Surgical Instrument Having a Third Example of a Mechanical Lockout Assembly FIGS. 11A-11B show a fourth exemplary ultrasonic surgical instrument (410) including a third mechanical lockout assembly (416). FIG. 11A of the present example shows that instrument (410) comprises a first modular assembly (412), a second modular assembly (414), an end effector (418), an ultrasonic blade (420), a clamp pad (422), a clamp pad assembly (424), a handle assembly (426), a shaft assembly (428), a body (430), a finger grip ring (432), one or more energy control buttons (434), an ultrasonic transducer (436), a proximal outer sheath (438), a waveguide (442), a distal outer sheath (448), a plug (452), a thumb grip ring (456), a clamp arm assembly (468), a distal face (472), a longitudinal pathway (478), an elongated arm (482), a plurality of pins (486), and an arm (490).

FIGS. 11A-11B show first modular assembly (412) configured to be removably coupled with second modular assembly (414). As shown, first modular assembly (412) includes handle assembly (426), ultrasonic transducer (436), energy control button (434), and proximal outer sheath (438). Ultrasonic transducer (436) is supported by first modular assembly (412). Waveguide (442) is acoustically coupled with ultrasonic transducer (436). Second modular assembly (414) includes waveguide (442), clamp arm assembly (468), distal outer sheath (448), and at least a portion of end effector (418). End effector (418) extends distally from a distal end portion of second modular assembly (414).

FIGS. 11A-11B show mechanical lockout assembly (416) configured to enable switching between at least an unlocked configuration and a locked configuration. Mechanical lockout assembly (416) locks out instrument (410), so that instrument (410) cannot be activated by energy control buttons (434). Mechanical lockout assembly (416) includes a barrier (444) that includes a body portion (446) and at least one aperture (450). Barrier (444) is operatively coupled to shaft assembly (428) using a coupling mechanism (453), such that barrier (444) translates between the locked configuration and the unlocked configuration. Barrier (444) may be made from any material having lateral flexibility yet also have substantial column strength to be urged longitudinally along instrument (410). Handle assembly (426) includes a passageway (455) extending between energy control button (434) and a switch (458). While two energy control buttons (434) and two switches (458) are shown, more or fewer energy control buttons (434) and switches (458) are envisioned, for example, one or three. While not shown, the number of energy control button (434) and switches (458) may vary.

FIG. 11A shows instrument (410) in the locked configuration, where first modular assembly (412) and second modular assembly (414) are partially coupled together, such that the operator is physically prevented from activating instrument (410) using energy control buttons (434). As shown, mechanical lockout assembly (416) prevents activation of energy control buttons (434) by obstructing completion of the electrical circuit until the shaft assembly (428) is fully seated. Body portion (446) is disposed between energy control button (434) and switch (458), thereby providing a physical obstruction that prevents energy control button (434) from actuating switch (458). Mechanical lockout assembly (416) also includes a resilient element, shown as a spring (460), to return mechanical lockout assembly (416) to the locked configuration, when shaft assembly (428) is subsequently removed. When second modular assembly (412), which may be a disposable portion of instrument (410), in inserted together with first modular assembly (412), which may be a reusable portion of instrument (410), barrier (444) translates proximally. As shown, the entire barrier (444) translates proximally. This translation of barrier (444) allows energy control buttons (434) to mechanically actuate switches (458) to activate instrument (410). At least one of energy control buttons (434) or switches (458) may enter into passageway (455).

FIG. 11B shows the unlocked configuration, where first modular assembly (412) and second modular assembly (414) are completely coupled together and the operator is able to activate instrument (410) using energy control buttons (434). In the unlocked configuration, apertures (450) are disposed between energy control buttons (434) and switches (458), enabling buttons (434) to actuate switches (458).

Figure 12:
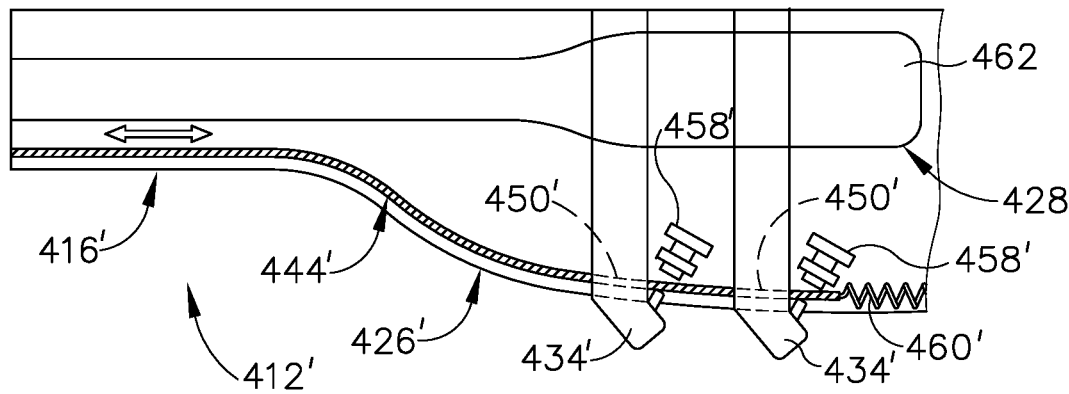
FIG. 12 depicts a schematic side sectional view of a portion of the instrument similar to FIG. 11A, but including a fourth exemplary mechanical lockout assembly in an unlocked configuration.

D. Fourth Exemplary Ultrasonic Surgical Instrument Having a Fourth Example of a Mechanical Lockout Assembly FIGS. 12-13B show various sectional views of another exemplary embodiment of a fourth mechanical lockout assembly (416'). FIG. 12 shows barrier (444') passing below acoustic drivetrain (462) and between energy control buttons (434') and switches (458') in handle assembly (426').

Figure 13A:
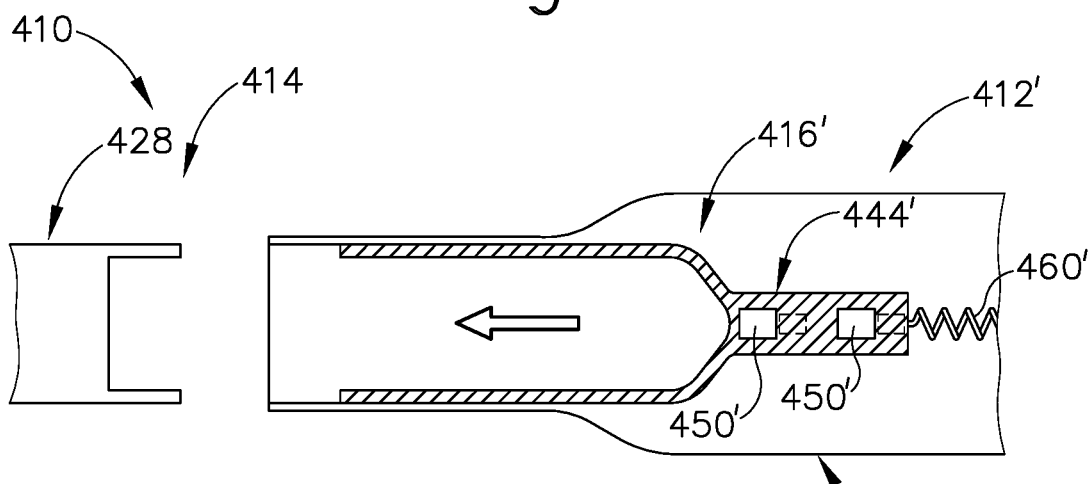
FIG. 13A depicts a schematic top sectional view of a portion of the instrument similar to FIG. 12 in a locked configuration.
Figure 13B:
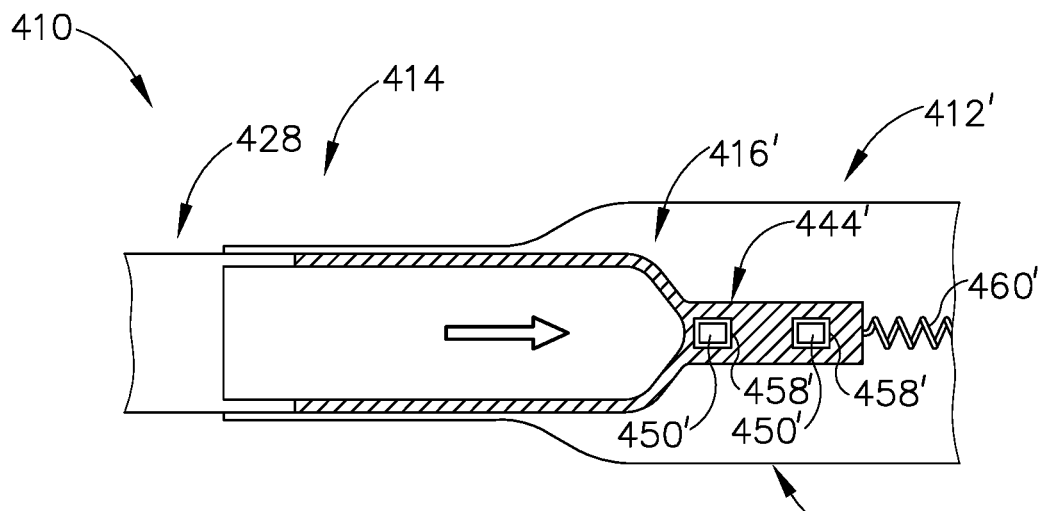
FIG. 13B depicts a schematic top sectional view of the instrument similar to FIG. 12, but in the unlocked configuration.

FIG. 13A shows that first modular assembly (412') may be a reusable portion, second modular assembly (414') may be a disposable portion, and spring (460') pushes barrier (444')

forward when in the locked configuration, preventing activation of instrument (410). Switches (458') are blocked from being pressed by energy control buttons (434') by barrier (444').

FIG. 13B shows where mechanical lockout assembly (416') is pressed inward by disposable second modular assembly (414'). Apertures (450'), shown as windows, are now positioned between switches (458') and energy control buttons (434'), enabling energy control buttons (434') to press through barrier (444') into switches (458') to activate instrument (410') in the unlocked configuration.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) a mechanical lockout assembly configured to switch between at least an unlocked configuration and a locked configuration, wherein in the locked configuration, the handle assembly and the clamp arm assembly are not completely coupled together and the operator is physically prevented from activating the instrument using an operator input feature, and wherein in the unlocked configuration, the clamp arm assembly and the shaft assembly are completely coupled together and the operator is able to activate the instrument using the operator input feature.

Example 2

The ultrasonic surgical instrument of Example 1, wherein in the locked configuration the mechanical lockout assembly prevents the operator input feature of rotating the clamp arm relative to the ultrasonic blade, thereby preventing the operator from clamping onto tissue by rotating the clamp arm relative to the ultrasonic blade

Example 3

The ultrasonic surgical instrument of any one or more of Examples 1 through 2, wherein the mechanical lockout assembly further includes a pin that pivotably couples the distal outer sheath with both the clamp arm assembly and the lockout member.

Example 4

The ultrasonic surgical instrument of any one or more of Examples 1 through 3, wherein the mechanical lockout assembly prevents the operator input feature of activating at least one energy control button disposed on the handle assembly preventing activation of the ultrasonic blade

Example 5

The ultrasonic surgical instrument of any one or more of Examples 1 through 4, wherein the mechanical lockout assembly further includes at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm relative to the ultrasonic blade, and wherein in the unlocked configuration, the lockout feature allows rotation of the clamp arm relative to the ultrasonic blade

Example 6

The ultrasonic surgical instrument of any one or more of Examples 1 through 5, wherein the lockout member uses the same rotation point as the clamp arm assembly

Example 7

The ultrasonic surgical instrument of any one or more of Examples 1 through 6, wherein the clamp arm assembly further includes at least one cutout portion, and wherein the lockout member is configured to move from the locked configuration to the unlocked configuration while being at least partially disposed within the cutout portion

Example 8

The ultrasonic surgical instrument of any one or more of Examples 1 through 7, wherein the cutout portion includes a protrusion to inhibit translation of the lockout member while in the locked configuration

Example 9

The ultrasonic surgical instrument of any one or more of Examples 1 through 8, wherein the lockout member moves distally away from the protrusion when moving from the locked configuration to the unlocked configuration.

Example 10

The ultrasonic surgical instrument of any one or more of Examples 1 through 9, wherein in the unlocked configuration, the clamp arm assembly freely rotates relative to the lockout member

Example 11

The ultrasonic surgical instrument of any one or more of Examples 1 through 10, wherein the clamp arm assembly includes an outer sheath, wherein the mechanical lockout assembly further includes at least one projection operatively coupled with a clamp arm assembly, wherein in the locked configuration the projection is not received by a corresponding recess in the outer sheath, the locked configuration preventing the operator input feature of rotating the clamp arm relative to the ultrasonic blade as the projection provides a hard stop preventing the clamp arm from pivoting toward the ultrasonic blade, and wherein in the unlocked configuration where the proximal outer sheath is coupled with the distal outer sheath, the projection is received by the corresponding recess in the distal outer sheath enabling the operator input feature of rotating the clamp arm assembly relative to the ultrasonic blade Example 12

The ultrasonic surgical instrument of any one or more of Examples 1 through 11, wherein the projection is a curvilinear projection that in the unlocked configuration is received by a curvilinear recess in the outer sheath Example 13

The ultrasonic surgical instrument of any one or more of Examples 1 through 12, wherein the handle assembly further includes the operator input feature, wherein the operator input feature includes at least one energy control button separated by a passageway from a switch within the housing, wherein the mechanical lockout assembly further includes a barrier that includes a body portion and at least one aperture that translates between the locked configuration and the unlocked configuration within the passageway, wherein in the locked configuration, the body portion is disposed within the passageway between the energy control button and the switch preventing the switch from activating the instrument, and wherein in the unlocked configuration, the aperture is disposed within the passageway between the energy control button and the switch enabling the switch to activate the instrument Example 14

The ultrasonic surgical instrument of any one or more of Examples 1 through 13, wherein the barrier includes a flexible member that is operatively coupled with the shaft assembly, and wherein the flexible element is pushed into the passageway such that in the locked configuration the flexible member extends between the energy control button and the switch Example 15

The ultrasonic surgical instrument of any one or more of Examples 1 through 14, wherein in the unlocked configuration, at least one of the energy control button or the switch extends at least partially through the aperture of the barrier and makes direct physical contact with the other of the energy control button or the switch through the aperture Example 16

The ultrasonic surgical instrument of any one or more of Examples 1 through 15, wherein a coupling mechanism attaches the barrier to the clamp arm assembly Example 17

The ultrasonic surgical instrument of any one or more of Examples 1 through 16, wherein a spring pushes the mechanical lockout assembly from the locked configuration to the unlocked configuration when the clamp arm assembly is removed from the handle assembly Example 18

An ultrasonic surgical instrument, comprising: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm relative to the ultrasonic blade, and wherein in the unlocked configuration, the lockout feature allows rotation of the clamp arm relative to the ultrasonic blade Example 19

The ultrasonic surgical instrument of any one or more of Examples 1 through 18, wherein the handle assembly includes a projection that displaces the lockout member distally when coupling the handle assembly with the clamp arm assembly Example 20

A method of operating an ultrasonic surgical instrument, wherein the ultrasonic surgical instrument comprises: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) a mechanical lockout assembly configured to switch between at least an unlocked configuration and a locked configuration, wherein the method comprises: (a) inhibiting the operator input feature from activating the instrument while in the locked configuration when the handle assembly and the clamp arm assembly are partially coupled together, wherein inhibiting rotation of the clamp arm provides instant feedback to an operator; (b) coupling the handle assembly and the clamp arm assembly completely together to disarm the locking assembly; and (c) activating the instrument using the operator input feature when in the unlocked configuration Example 21

The method of Example 20, wherein the inhibiting the operator input feature further includes the mechanical lockout assembly preventing the operator input feature of rotating the clamp arm relative to the ultrasonic blade that prevents the operator from clamping onto tissue Example 22

The method of any one or more of Examples 20 through 21, wherein the inhibiting the operator input feature further includes the mechanical lockout assembly preventing the operator input feature of activating at least one energy control button disposed on the handle assembly preventing the operator from activating the ultrasonic blade.

IV. Miscellaneous

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on April 2017issued as U.S. Pat. No. 11,045,275 on Jun. 29, 2021, the disclosure of which is incorporated by reference herein. Various suitable ways in which the teachings herein may be combined with the teachings of U.S. Pub. No. 2017/0105754, issued as U.S. Pat. No. 11,045,275 on Jun. 29, 2021, will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published on Apr. 20, 2017, issued as U.S. Pat. 11,020,200 on Jun. 1, 2021, the disclosure of which is incorporated by reference herein. Various suitable ways in which the teachings herein may be combined with the teachings of U.S. Pub. No. 2017/0105755, issued as U.S. Pat. No. 11,020,200 on Jun. 1, 2021, will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," filed on Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105788, issued as U.S. Pat. No. 10,893,914 on Jan. 19,2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) an ultrasonic transducer;
   (b) a handle assembly supporting the ultrasonic transducer, wherein the handle assembly includes:

(i) a housing, and
(ii) an operator input feature configured to selectively mechanically actuate from a first position to a second position to thereby activate the instrument in the second position;
(c) at least a portion of a shaft assembly distally extending from the handle assembly and including an ultrasonic blade acoustically coupled with the ultrasonic transducer;
(d) a clamp arm assembly including a clamp arm; and
(e) a mechanical lockout assembly configured to switch between at least an unlocked configuration and a locked configuration,
wherein in the locked configuration, the clamp arm assembly and the at least the portion of the shaft assembly are not completely coupled together and the mechanical lockout assembly prevents selective mechanical actuation of the operator input feature from the first position to the second position such that the operator is physically prevented from activating the instrument using the operator input feature, and
wherein in the unlocked configuration, the clamp arm assembly and the at least the portion of the shaft assembly are completely coupled together and the mechanical lockout assembly allows selective mechanical actuation of the operator input feature from the first position to the second position such that the operator is able to activate the instrument using the operator input feature.

2. The ultrasonic surgical instrument of claim 1, wherein in the locked configuration the mechanical lockout assembly prevents the operator input feature of rotating the clamp arm relative to the ultrasonic blade, thereby preventing the operator from clamping onto tissue by rotating the clamp arm relative to the ultrasonic blade.

3. The ultrasonic surgical instrument of claim 1, wherein the mechanical lockout assembly prevents the operator input feature of activating at least one energy control button disposed on the handle assembly preventing activation of the ultrasonic blade.

4. The ultrasonic surgical instrument of claim 1, wherein the mechanical lockout assembly further includes at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm relative to the ultrasonic blade, and wherein in the unlocked configuration, the lockout feature allows rotation of the clamp arm relative to the ultrasonic blade.

5. The ultrasonic surgical instrument of claim 4, wherein the at least one lockout member uses the same rotation point as the clamp arm assembly.

6. The ultrasonic surgical instrument of claim 4, wherein the clamp arm assembly further includes at least one cutout portion, and wherein the at least one lockout member is configured to move from the locked configuration to the unlocked configuration while being at least partially disposed within the at least one cutout portion.

7. The ultrasonic surgical instrument of claim 6, wherein the at least one cutout portion includes a protrusion to inhibit translation of the at least one lockout member while in the locked configuration.

8. The ultrasonic surgical instrument of claim 4, wherein in the unlocked configuration, the clamp arm assembly freely rotates relative to the at least one lockout member.

9. The ultrasonic surgical instrument of claim 1, wherein the clamp arm assembly includes an outer sheath, wherein the mechanical lockout assembly further includes at least one projection operatively coupled with a clamp arm assembly, wherein in the locked configuration the projection is not received by a corresponding recess in the outer sheath, the locked configuration preventing the operator input feature of rotating the clamp arm relative to the ultrasonic blade as the projection provides a hard stop preventing the clamp arm from pivoting toward the ultrasonic blade, and wherein in the unlocked configuration the projection is received by the corresponding recess in the outer sheath enabling the operator input feature of rotating the clamp arm assembly relative to the ultrasonic blade.

10. The ultrasonic surgical instrument of claim 9, wherein the projection is a curvilinear projection that in the unlocked configuration is received by a curvilinear recess in the outer sheath.

11. The ultrasonic surgical instrument of claim 1, wherein the operator input feature includes at least one energy control button separated by a passageway from a switch within the housing, wherein the mechanical lockout assembly further includes a barrier that includes a body portion and at least one aperture that translates between the locked configuration and the unlocked configuration within the passageway, wherein in the locked configuration, the body portion is disposed within the passageway between the energy control button and the switch preventing the switch from activating the instrument, and wherein in the unlocked configuration, the aperture is disposed within the passageway between the energy control button and the switch enabling the switch to activate the instrument.

12. The ultrasonic surgical instrument of claim 11, wherein the barrier includes a flexible member that is operatively coupled with the shaft assembly, and wherein the flexible element is pushed into the passageway such that in the locked configuration the flexible member extends between the energy control button and the switch.

13. The ultrasonic surgical instrument of claim 11, wherein in the unlocked configuration, at least one of the energy control button or the switch extends at least partially through the aperture of the barrier and makes direct physical contact with the other of the energy control button or the switch through the aperture.

14. The ultrasonic surgical instrument of claim 11, wherein a coupling mechanism attaches the barrier to the clamp arm assembly.

15. The ultrasonic surgical instrument of claim 1, wherein a spring pushes the mechanical lockout assembly to the locked configuration from the unlocked configuration.

16. An ultrasonic surgical instrument, comprising:
(a) an ultrasonic transducer;
(b) a handle assembly supporting the ultrasonic transducer, wherein the handle assembly includes a housing
(c) at least a portion of a shaft assembly distally extending from the handle assembly and including an ultrasonic blade acoustically coupled with the ultrasonic transducer;
(d) a clamp arm assembly including a first clamp arm configured to be selectively actuated relative to the handle assembly by an operator and a second clamp arm configured to support a clamp pad thereon, wherein the first and second clamp arms are pivotally connected such that selective actuation of the first clamp arm directs the second clamp arm toward the ultrasonic blade; and (e) at least one lockout member having a body that includes a lockout feature configured to move relative to the first clamp arm between at least an unlocked configuration and a locked configuration, wherein in the locked configuration, the body of the lockout member is in a locked position that prevents movement of the first clamp arm relative to the handle assembly to thereby prevent movement of the second clamp arm relative to the ultrasonic blade, wherein in the locked configuration, the at least the portion of the shaft assembly and the clamp arm assembly are only partially coupled together physically preventing the operator from actuating the first clamp arm, and wherein in the unlocked configuration, the at least the portion of the shaft assembly and the clamp arm assembly are completely coupled together enabling the operator to actuate the first clamp arm, and wherein in the unlocked configuration, the body of the lockout member is in an unlocked position that allows movement of the first clamp arm relative to the handle assembly to thereby allow movement of the second clamp arm relative to the ultrasonic blade.

17. An ultrasonic surgical instrument, comprising:
(a) an ultrasonic transducer;
(b) a handle assembly supporting the ultrasonic transducer, wherein the handle assembly includes:
 (i) an operator input feature, and
 (ii) a switch, wherein the switch is configured to be selectively actuated by the operator input feature;
(c) at least a portion of a shaft assembly distally extending from the handle assembly and including an ultrasonic blade acoustically coupled with the ultrasonic transducer
(d) a clamp arm assembly including a clamp arm; and
(e) a mechanical lockout assembly including a barrier configured to move between at least an unlocked configuration and a locked configuration, wherein in the locked configuration, the barrier is disposed in a first position to block movement of the operator input feature thereby preventing the switch from activating the ultrasonic transducer, and wherein in the unlocked configuration, the barrier is in a second position to enable movement of the operator input feature thereby enabling the switch to activate the ultrasonic transducer.

18. The ultrasonic surgical instrument of claim 17, wherein in the locked configuration, the at least the portion of the shaft assembly and the clamp arm assembly are only partially coupled together physically preventing the operator from activating the ultrasonic transducer using the operator input feature, and wherein in the unlocked configuration, the at least the portion of the shaft assembly and the clamp arm assembly are completely coupled together enabling the operator to activate the ultrasonic transducer using the operator input feature.

19. The ultrasonic surgical instrument of claim 18, wherein the handle assembly further includes a passageway between the operator input feature and the switch, wherein the barrier is positioned within the passageway and configured to move within the passageway from the first position to the second position.

\* \* \* \* \*